(12) United States Patent
Holmes et al.

(10) Patent No.: US 6,626,566 B2
(45) Date of Patent: Sep. 30, 2003

(54) COMPOUNDS FOR ELECTRONIC DEVICES

(75) Inventors: Andrew Bruce Holmes, Cambridge (GB); Stephen Carl Moratti, Cambridge (GB); Xiao-Chang Li, Union City, CA (US); Henning Sirringhaus, Cambridge (GB); Arno Kraft, Dusseldorf (DE); Michael Mark Murray, Cork (IE)

(73) Assignee: Cambridge Display Technology Limited, Cambridge (GB)

( * ) Notice: Subject to any disclaimer, the term of this patent is extended or adjusted under 35 U.S.C. 154(b) by 0 days.

(21) Appl. No.: 10/155,823

(22) Filed: May 24, 2002

(65) Prior Publication Data

US 2003/0088112 A1 May 8, 2003

Related U.S. Application Data

(63) Continuation of application No. 09/508,035, filed as application No. PCT/GB98/02672 on Sep. 4, 1998, now Pat. No. 6,403,809.

(30) Foreign Application Priority Data

Sep. 5, 1997 (GB) .............................................. 9718919
Jul. 8, 1998 (GB) .............................................. 9814814

(51) Int. Cl.$^7$ .......................... G02F 1/136; H01L 29/04; C08G 75/00

(52) U.S. Cl. ........................ 362/800; 257/59; 528/380; 349/42

(58) Field of Search ............................ 362/800; 257/59; 528/380; 349/42

(56) References Cited

U.S. PATENT DOCUMENTS

| | | | | |
|---|---|---|---|---|
| 4,639,328 A | | 1/1987 | Krause et al. ......... 252/299.61 |
| 4,663,001 A | | 5/1987 | Lazzaroni et al. ............. 204/78 |
| 5,210,217 A | * | 5/1993 | Albarella et al. ............ 548/527 |
| 5,412,105 A | * | 5/1995 | Ito et al. ........................ 549/4 |
| 5,432,286 A | | 7/1995 | Cabrera et al. ............. 546/270 |
| 5,519,147 A | * | 5/1996 | Swager et al. ................ 549/59 |
| 5,734,065 A | * | 3/1998 | Saika ........................... 549/59 |
| 6,130,339 A | | 10/2000 | Tan et al. ...................... 549/50 |
| 6,166,172 A | * | 12/2000 | McCullough et al. ....... 528/380 |
| 6,479,838 B2 | * | 11/2002 | Morosawa ................... 257/72 |
| 6,525,341 B1 | * | 2/2003 | Tsujimura et al. ............ 257/59 |
| 6,529,251 B2 | * | 3/2003 | Hibino et al. ................. 349/42 |

OTHER PUBLICATIONS

Cervini et al., "Synthesis of New Conjugated Thiophene Polymers," Synthetic Metals, 76 (1996) pp. 169–171.
Rutherford et al., "Poly(2,5–ethynylenethiophenediylethynylenes), Related Heteroaromatic Analogues, and Poly-(thieno[3,2–b]thiophenes), Synthesis and Thermal and Electrical Properties", Macromolecules, vol. 25, No. 9, Apr. 27, 1992, pp. 2294–2306.
Kossmehl et al., Über Polyarylenalkenylene und Polyheteroarylenalkenylene, Makromolekulare Chemi, vol. 183, No. 11, Nov. 1982, pp. 2771–2786.
Arbizzani et al., "N– And P–Doped Polydithieno[3,4–B:3', 4'–D] Thiophene: A Narrow Band Gap Polymer For Redox Supercapacitors," Electrochimica Acta, vol. 40, No. 12, Sep. 1995, pp. 1871–1876.
De Jong et al., "The Synthesis, Oxidation and Electronic Spectra of Four Dithienothiophenes," J. Org. Chem., vol. 36, No. 12, 1971, pp. 1645–1648.
Sirringhaus et al., "Bis(dithienothiophene) Organic Field–Effect Transistors With A High On/Off Ratio," Applied Physics Letters, Dec. 29, 1997, AIP, USA, vol. 71, No. 26, pp. 3871–3873.
Sato et al., CA117:16498, 1992.
Kobayashi, CA112: 55655, 1990.
Mazaki et al., CA118: 59068, 1993.
Sirringhaus et al., CA128: 161412, 1998.
Klemm et al., CA74: 64139.

* cited by examiner

*Primary Examiner*—Deborah C. Lambkin
(74) *Attorney, Agent, or Firm*—Finnegan, Henderson, Farabow, Garrett & Dunner, LLP

(57) ABSTRACT

The present invention provides a compound or complex comprising at least two moieties, each moiety being comprised of two or more thiophenes fused directly to each other. Also provided is a method for the production of the compounds of the present invention, which method comprises the coupling of one fused thiophene derivative to another fused thiophene derivative.

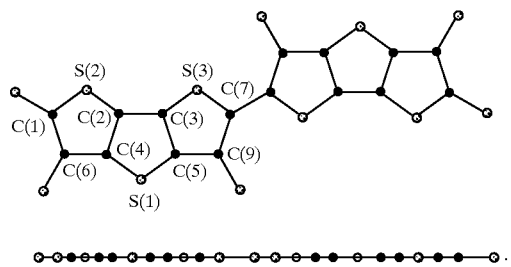

25 Claims, 9 Drawing Sheets

COMPOUNDS FOR ELECTRONIC DEVICES

This is a continuation of application Ser. No. 09/508,035, filed May 30, 2000, U.S. Pat. No. 6,403,809 which is a national stage of PCT/GB98/02672 filed Sep. 4, 1998, which claims priority from GB 9718919.5 filed Sep. 5, 1997 and GB 9814814.1 filed Jul. 8, 1998, all of which are incorporated herein by reference.

The present invention is concerned with conjugated organic compounds that can be used in electronic devices. In particular, fused thiophene oligomers or polymers can be used to fabricate thin-film transistors (TFTs) of field-effect transistors (FETs).

Organic semiconductors that consist of conjugated oligomers or polymers are subject of considerable current research interest, due to their fundamental opto-electronic physics and their potential applications in photo-diode (see reference 1), light-emitting devices (LEDs) (see reference 2) and thin film transistors (TFTs) (see reference 3) etc. The judicious choice of conjugated segments and their various combinations to form different length oligomers or polymers allows for sophisticated fine tuning of such molecular semiconductors, giving rise to surprisingly useful properties.

Pioneered by Garnier and his co-workers, oligomers of thiophenes ranging from tetramers to octamers have been explored as active materials for TFTs that hold great promise in the fabrication of smart cards and flexible flat-panel displays (see references 4–6). The field effect charge mobility of thiophene oligomers was found to increase with conjugation length and then level off after the hexamer. Longer conjugation length seems to incur processing and purification problems as well as difficulty to achieve long range molecular ordering, and thus adversely affect field effect mobility and on/off ratio.

Soluble regioregular poly(3-hexylthiophene) has very recently shown high mobility ($10^{-5}$ to 0.045 cm$^2$/Vs) (see reference 7), although its on/off ratio was rather low (10 to $10^3$) for reasons mentioned above. Therefore, the large majority of the past work into organic TFT materials has been concentrated on the hexamer of thiophene (or sexithiophene, a-hexathienyl, a-6T) and its alkylated derivatives. As a result, TFTs with mobilities of 0.03 cm$^2$V$^{-1}$s$^{-1}$ and on/off ratios of more than $10^6$ were achievable. The direction of high mobility in sexithiophene TFTs has been revealed to be parallel to the substrate and perpendicular to the long axis of the thiophene oligomer, indicating the importance of $\pi$ stacking to the contribution of charge mobility.

Katz et al (see reference 8) have recently successfully explored another high mobility (0.04 cm$^2$V$^{-1}$s$^{-1}$) organic TFT material, bis(benzodithiophene). The benzofused thiophenes may create greater overlap of the $\pi$-conjugated units though detailed crystalline structure was not given. Commercially available pentacene, a more advanced fused-ring compound, has received much less attention compared with thiophene oligomers in the past, probably because only low mobilities of 0.002 (see reference 9) or 0.009 cm$^2$V$^{-1}$s$^{-1}$ (see references 10, 11) were achieved.

Pentacene TFTs prepared by molecular beam deposition have recently shown high mobility (0.03 cm$^2$V$^{-1}$s$^{-1}$). Using purer material and a slower deposition rate, workers raised pentacene TFTs to a record high mobility of 0.3–0.7 cm$^2$V$^-$$_1$s$^{-1}$ (see references 12, 13). The high mobility has been associated both with $\pi$ stacking and the macroscopic single-crystal nature of sublimed pentacene films (see reference 14). Most organic materials suffer from poor "On/Off" characteristics ($10^2$–$10^5$) and high threshold slopes.

An object of the present invention is to solve the above problems associated with prior art materials and devices. Accordingly, the present invention provides a compound or complex comprising at least two moieties, each moiety being comprised of two or more thiophenes fused directly to each other. In the context of this invention the term moiety is intended to extend to different parts of a single monomeric molecule and also repeating units of a dimer, oligomer or polymer.

The present invention also provides a method for the production of a compound as defined above, which method comprises the coupling of one fused thiophene derivative to another fused thiophene derivative.

The present invention further provides an electric, electronic, or optoelectronic component or device comprising a compound as defined above.

The invention will be described in further detail by way of example only, with reference to the accompanying drawings, in which.

Figure 1:
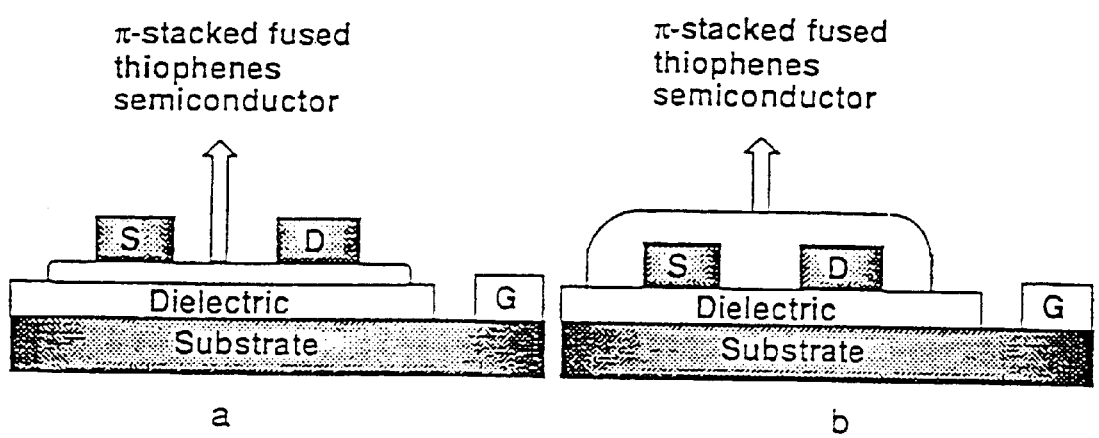
FIG. 1 shows the configuration of top-contact TFTs (a) and bottom-contact TFTs (b)

The present invention uses organic semiconductors based on fused thiophenes in which the use of a thin layer of the material enables the fabrication of solid state hetero-structural devices for instance, thin-film transistors (TFTs) with high performance. The organic semiconductors consist of oligomers or polymers based on fused thiophenes, which allow a maximal intermolecular $\pi$ overlapping to form compressed $\pi$ stacks in a supramolecular structure. High field-effect mobility and high On/Off ratio can therefore be achieved using this sort of organic semiconductor as an active material.

The present invention provides a means to design and synthesise organic semiconductors with both high mobilities and On/Off ratios used for use in high performance TFTs or FETs. The fused thiophenes, typically dithieno [3,2-b:2', 3'-d] thiophene are employed as building blocks for oligomers or polymers. The fused thiophenes not only provide a planar conjugated segment but also a sulphur rich source, which may adjust molecular structure and ordering. High field effect mobilities of 0.05 cm$^2$V$^{-1}$s$^{-1}$ and high On/Off ratios of more than $10^8$ have been achieved. Specifically X-ray analysis of a single crystal of α,α'-bis(dithieno[3,2- b:2',3'-d] thiophene) shows for the first time a face to face π stacking with the shortest itnerplanar distance of 3.56 Å. In this regard, even high mobility could be achieved if a macroscopic single crystal of this material could be realised during device fabrication.

This invention refers to the synthesis of novel fused heterocyclic ring compounds, their oligomers and polymers and their application as active materials in electronic devices, specifically thin film transistors. The fused heterocycles (more specifically thiophenes) may consist of two, three, four and five-fused thiophenes, preferably the three fused thiophenes (Scheme 1). Specifically the fused thiophene "dimer" 5 exemplifies the invention. In order to render the conjugated oligomers or polymers into solution processable form solubilising side chains may be attached or deposition of films may take place from solution using precursor materials.

Solubilising groups can have an advantageous effect on solution processability and supramolecular order in the active layer of a device. They may be attached at various positions on the heterocyclic ring to afford solution-processable organic materials. Solution processability plays an important part in controlling the morphology of the final thin film. Oligometric and polymeric substances may be selected from one of the following categories (Scheme 1). Monomeric units may also be selected from the representative examples shown in Scheme 1:

Scheme 1

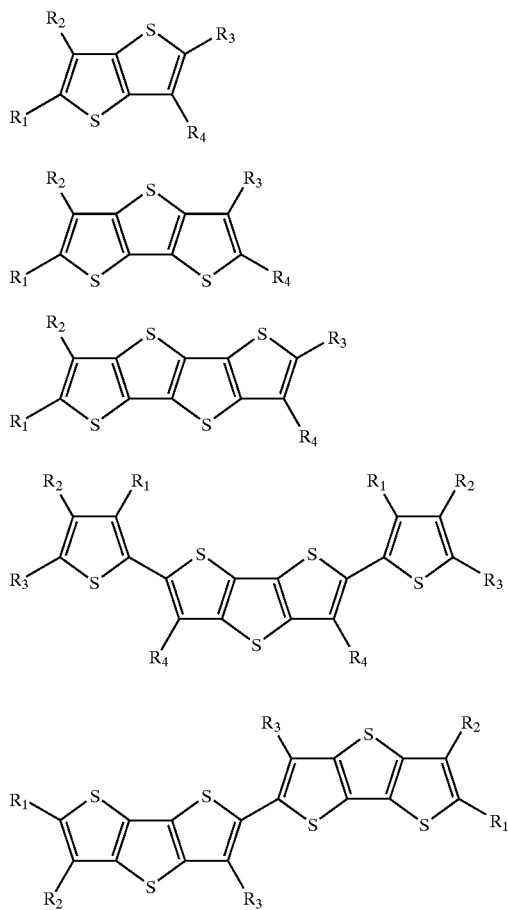

In Scheme 1, $R_1$, $R_2$, $R_3$ and $R_4$ may be selected from any combination of the following H, $(CH_2)_nCH_3$, $O(CH_2)_nCH_3$, $S(CH_2)_nCH_3$, or a branched chain derivative carrying aryl, alkyl or heterocyclic substituents or other solubilising side chain alkyl, aryl or heterocyclic substituents. $R_1$ may also be COOH, triazole, tetrazole or a derivative thereof.

Preferred oligomers include 4 ($R_1=C_8H_{17}$, $R_2=R_3=R_4=$H); 5 ($R_1=C_6H_{13}S—$, $R_2=R_3=H$); 5 ($R_1=C_8H_{17}$, $R_2=R_3=H$); 5 ($R_1=C_{10}H_{21}S—$, $R_2=R_3=H$); 5 ($R_1=C_{12}H_{25}$, $R_2=R_3=H$); 5 ($R_1=C_{12}H_{25}S—$, $R_2=R_3=H$); 2 ($R_1=COOH$, $R_2=R_3=R_4=H$); and 2 ($R_1=COOH$, $R_2=R_3=H$, $R_4=C_8H_{17}$).

Polymeric units may be selected from the structure 6 and a selection of repeat units from scheme 2:

─[Fused thiophene building block]$_n$─ n=1,2,3,4,>4

Scheme 2

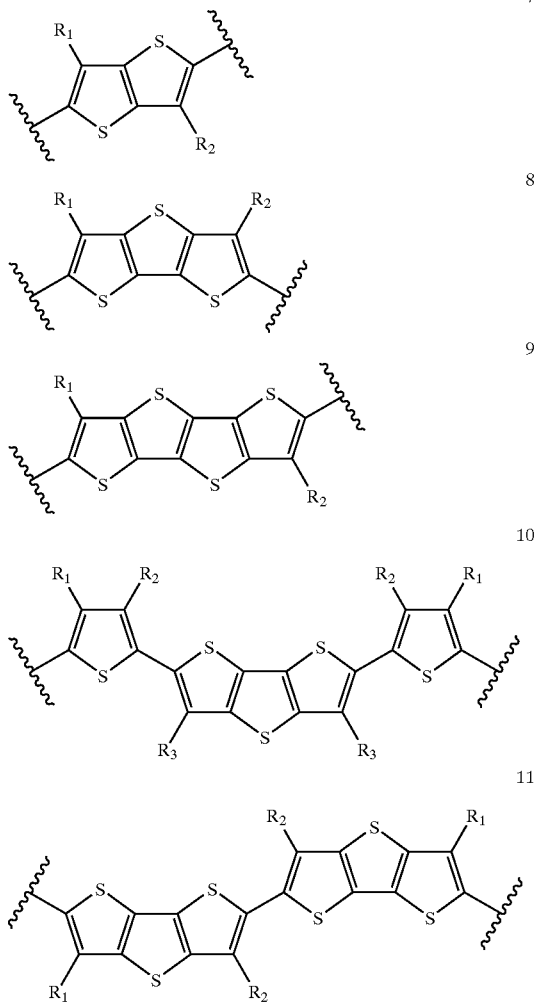

In scheme 2, $R_1$, $R_2$, and $R_3$ may be selected from any combination of the following H, $(CH_2)_nCH_3$, $O(CH_2)_nCH_3$, $S(CH_2)_nCH_3$, or a branched chain derivative carrying aryl, alkyl or heterocyclic substituents or other solubilising side chain alkyl, aryl or heterocyclic substituents. $R_1$ may also be COOH, triazole, tetrazole or a derivative thereof.

Preferably, polymers 6 will carry the repeat unit 10 ($R_1=H$, $R_2=$alkyl, $R_3=H$) and 10 ($R_1=R_2=$alkyl, $R_3=H$).

Supramolecular order in dendritic complexes of transport material

Figure 9:
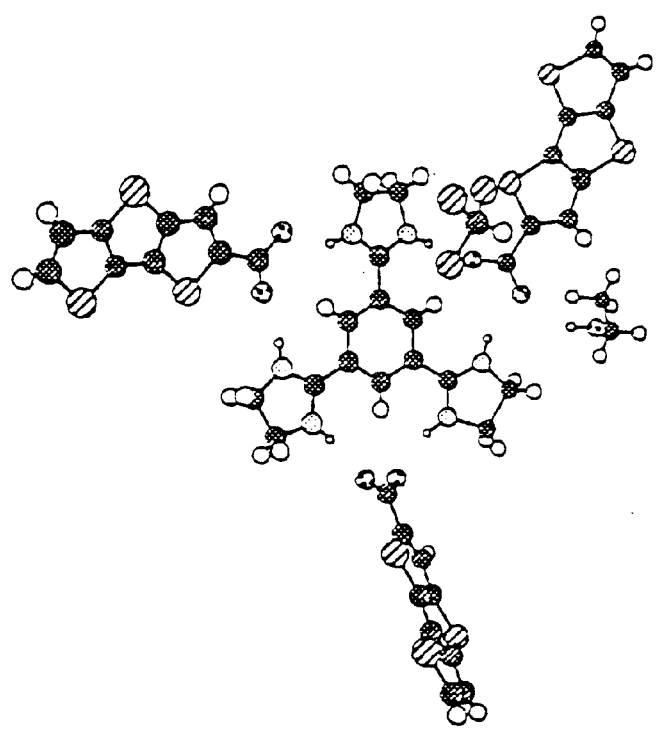
FIG. 9 shows the x-ray structure of the complex 12.

Recent work by Kraft et al (see reference 27) has shown that self assembled dendrimers provided by hydrogen bonding between aryl carboxylic acids and poly-imidazole bases can form large planar complexes. The complex 12 of the carboxylic acid 2 ($R_1$=COOH, $R_2$=$R_3$=$R_4$=H) show in scheme 3 with tris (4,5-dihydroimidazol-2-yl) benzene gave the complex shown in scheme 3 (see also FIG. 9). This surprisingly shows considerable order, as evidence by Synchrotron X-ray analysis. Such order may lend itself to the formation of highly ordered films for FETs, and furthermore the supramolecular ordering may be manifested in high mobility transistor materials.

Further supramolecular assembled complexes analogous to the complex 12 of scheme 3 based on 2 ($R_1$=$C_8H_{17}$ or $C_6H_{13}$S—, or $C_6H_{13}$S—, $R_2$=$R_3$=H, $R_4$=COOH) have been made. A specific embodiment is the complex 13 derived from 2 ($R_1$=$C_8H_{17}$, $R_2$=$R_3$=H, $R_4$=COOH) and 1,3,5-tris (dihydroimidazole). This shows interesting mesophase behaviour, which will contribute to the control of supramolecular order. In the present invention exploitation of supramolecular order allows special processing and orientation of materials to achieve high mobilities in FETs.

In a particular embodiment α,α'-bis (dithieno [3,2-b:2', 3'-d] thiophene (BDT) (5 ($R_1$=$R_2$=$R_3$=H)), the "dimer" of 2 ($R_1$=$R_2$=$R_3$=$R_4$=H), has been synthesised and fully characterised. The fused thiophene compound, dithieno [3,2-b:2', 3'-d] thiophene (2 ($R_1$=$R_2$=$R_3$=$R_4$=H)) was synthesised according to a published protocol, starting from 3-bromothiophene (see reference 15). The "dimerisation" was carried out through the coupling reaction of a-lithiated monomer 3 using ferric acetylacetonate as an oxidative coupling reagent (Scheme 4). Other coupling reagents, e.g. $CuCl_2$, also caused coupling. BDT (5 ($R_1$=$R_2$=$R_3$=H)) was just soluble enough in boiling toluene or hot DMF for recrystallisation, and slightly soluble in THF. (2 g/1), allowing for great convenience in purification and identification by $^1$H NMR. Its microcrystal power has a gold like lustre and shows no chemical change in ambient conditions within a test time of 2 months. Various characterisations, $^1$H NMR, UV, FTIR, microanalysis and high resolution mass spectroscopy, are all in agreement with the structure of 5 ($R_1$=$R_2$=$R_3$=H).

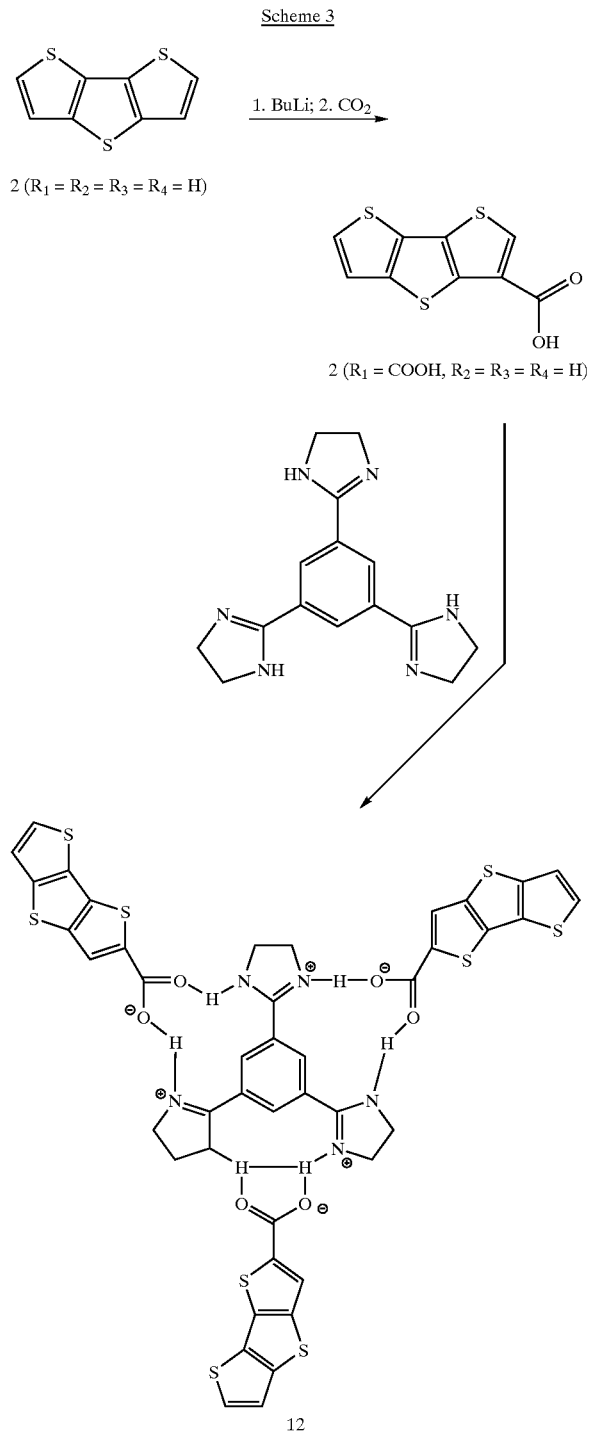

Scheme 3

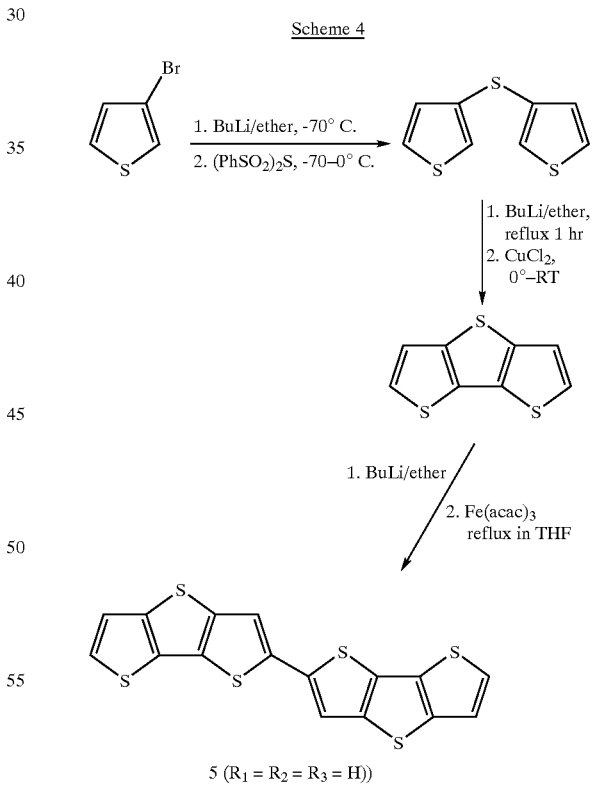

Scheme 4

For further purification, the dimer BDT was readily sublimed at 2001 C. under vacuum ($10^{-4}$–$10^{-5}$ mmHg) in a gradient sublimation tube (see reference 16). The resulting sample of BDT has a finer crystalline size and lighter colour than before sublimation.

BDT was found to fluoresce with an orange colour in the solid state and blue in dilute solution under UV irradiation.

Figure 2:
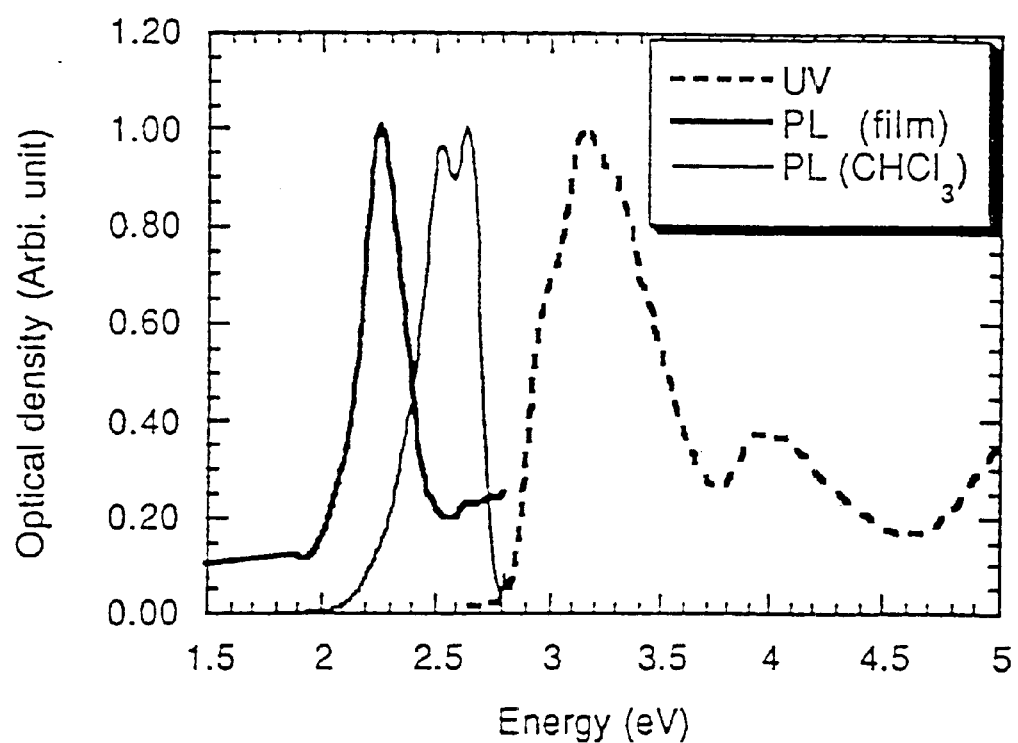
FIG. 2 shows a UV absorption spectrum and emission spectrum of BDT.

FIG. 2 shows the UV absorption and emission spectra for the dimer. A π–π* gap of 2.8 eV in dilute solution (CHCl$_3$ solvent) was observed from the absorption edge or from the photoluminescent emission peak, and 2.3 eV π–π* gap in solid film was obtained from its solid film emission peak. The emissive properties of BDT may be exploited in organic electroluminescent devices.

Figure 3:
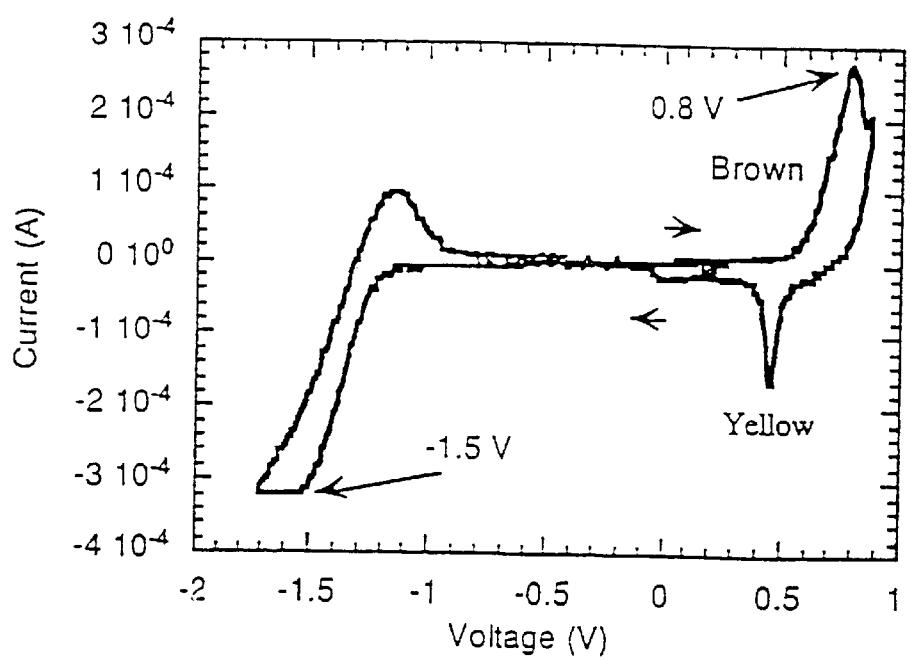
FIG. 3 shows a cyclic voltammogram of a BDT film on Au commencing from 0->0.9->0->1.7->0 V (Et$_4$BF$_4$ in CH$_3$CN, 0.1 M)

Cyclic voltammetric measurement of the thin film of BDT revealed that both electrons and holes can be injected into the film, or in other words, BDT can be both n-doped or p-doped. FIG. 3 shows a full sweep cyclic voltammogram for BDT film on Au coated glass substrate. A distinct colour change from yellow to brown to yellow was observed upon oxidative sweeping from 0 to 0.9 to 0 V (versus FOC), indicating an electrochemical quasi-reversible process upon p-doping (or hole injection) that may be related to the formation of a radical cation (see reference 17). A similar electrochemical process was noticed during the reduction sweep, suggesting a reversible n-doping (or election injection) process. No apparent colour change was observed during the reduction sweep. According to tis redox peak positions, the HOMO/LUMO level of −5.6 eV/−3.3 eV was estimated for BDT, indicating a band gap of 2.3 eV from electrochemical measurement that is in good agreement with its solid state band gap measured from its electronic spectroscopic measurements. When the oxidation potential was larger than 1.2 V, a two-electron injection feature was observed, and the BDT colour changed to dark green or black, indicting perhaps the formation of a di-cation which is quite universal for conjugated polymers (see references 17,18).

Figure 4:
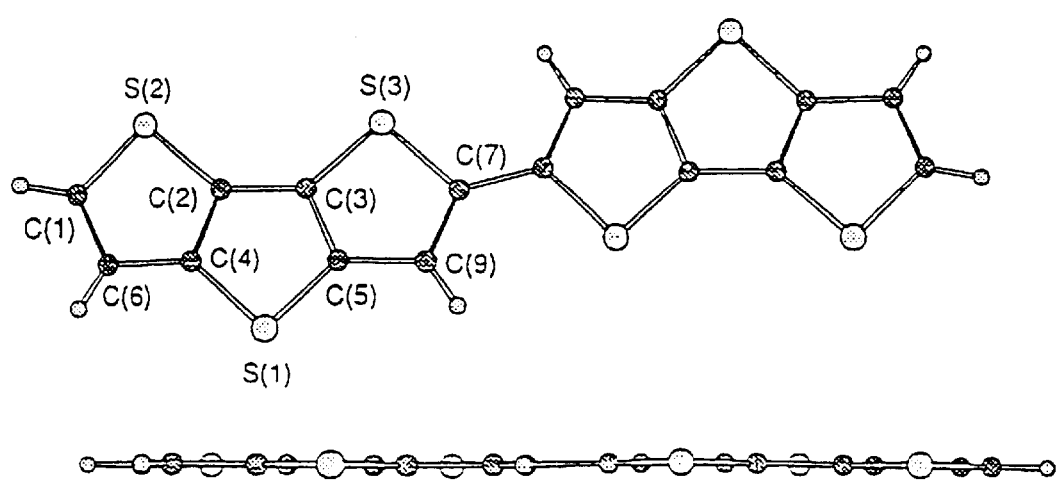
FIG. 4 shows the front and side view of a BDT molecule with numbering.

A single crystal of BDT has been grown by the inventors by very slow cooling down of the saturated solution of BDT in toluene. Full crystallographic data were collected by a Synchrotron radiation source detailed below, as the single crystal was relatively small. Similar to α-6T and α-octathiophene, BDT crystallises in the monoclinic system, but has a C2/c space group. It is apparent that BDT has the greatest density, perhaps due to the high ratio of S/C in the molecule, or its highly packed structure. The BDT molecule has a completely planar conformation (see FIG. 4), like 6 T and pentacene.

TABLE 1

Crystallographic data of BDT (collected at 160 ± 2 K)

| | |
|---|---|
| Chemical formula | C$_{16}$H$_6$S$_6$ |
| Formular weight | 390.57 |
| Wavelength | 0.68790 Å |
| Crystal system | Monoclinic |
| Space group | C2/c |
| Unit cell dimensions | a = 33.689(2) Å, α = 90° |
| | b = 3.8834(2) Å, β = 101.0932(2)° |
| | c = 11.1055(5) Å, γ = 90° |
| Volume | 1425.75(13) Å$^3$ |
| Z | 4 |
| Density (calculated) | 1.820 Mg/m$^3$ |
| Absorption coefficient | 0.948 mm$^{-1}$ |
| F(000) | 792 |
| Crystal size | 0.07 × 0.02 × 0.02 mm |
| Q range for data collection | 3.58 to 26.89° |
| Index ranges | −42 < h < 34, −4 < k < 5, −14 < l < 13 |
| Reflections collected | 1272 |
| Independent reflections | 813 (R$_{int}$ = 0.0429) |
| Absorption correction | Sadabs |
| Refinement method | Full-matrix least-squares on F$^2$ |
| Data/restraints/parameters | 813/0/100 |
| Goodness-of-fit on F$^2$ | 1.043 |

TABLE 1-continued

Crystallographic data of BDT (collected at 160 ± 2 K)

| | |
|---|---|
| Final R indices [I > 2 s(I)] | R1 = 0.078, wR2 = 0.1265 |
| R indices (all data) | R1 = 0.0556, wR2 = 0.1314 |
| Large diff. peak and hole | 0.44 and −0.490 eÅ$^3$ |

TABLE 2

Bond lengths [Å] and angles [°] for BDT

| | | | |
|---|---|---|---|
| S(1)-C(4) | 1.73(4) | S(1)-C(S) | 1.739(4) |
| S(2)-C(1) | 1.724(4) | S(2)-C(2) | 1.726(4) |
| C(9)-C(7) | 1.377(6) | C(9)-C(5) | 1.410(5) |
| C(9)-H(9) | 0.95 | C(6)-C(1) | 1.356(6) |
| C(6)-C(4) | 1.428(6) | C(6)-H(6) | 0.95 |
| C(5)-C(3) | 1.392(6) | C(4)-C(2) | 1.378(6) |
| C(3)-C(2) | 1.426(5) | C(3)-S(3) | 1.724(4) |
| C(1)-H(1) | 0.95 | S(3)-C(7) | 1.750(4) |
| C(7)-C(7)* | 1.445(7) | | |
| C(4)-S(1)-C(5) | 90.0(2) | C(1)-S(2)-C(2) | 90.7(2) |
| C(7)-C(9)-C(5) | 112.0(3) | C(7)-C(9)-H(9) | 124.0(2) |
| C(5)-C(9)-H(9) | 124.0(2) | C(1)-C(6)-C(4) | 110.3(4) |
| C(1)-C(6)-H(6) | 124.9(2) | C(4)-C(6)-H(6) | 124.9(2) |
| C(3)-C(5)-C(9) | 113.7(4) | C(30)-C(5)-S(1) | 112.9(3) |
| C(9)-C(5)-S(1) | 133.4(3) | C(2)-C(4)-C(6) | 113.8(4) |
| C(2)-C(4)-S(1) | 113.3(3) | C(6)-C(4)-S(1) | 132.9(3) |
| C(5)-C(3)-C(2) | 111.7(3) | C(5)-C(3)-S(3) | 111.1(3) |
| C(2)-C(3)-S(3) | 137.2(3) | C(4)-C(2)-C(3) | 112.0(4) |
| C(4)-C(2)-S(2) | 111.1(3) | C(3)-C(2)-S(2) | 136.9(3) |
| C(6)-C(1)-S(2) | 114.2(3) | C(6)-C(I)-H(1) | 122.9(2) |
| S(2)-C(1)-H(1) | 122.9(2) | C(3)-S(3)-C(7) | 91.4(2) |
| C(9)-C(7)-C(7)* | 128.4(5) | C(9)-C(7)-S(3) | 111.9(3) |
| C(7)*-C(7)-S(3) | 119.7(4) | | |

*Symmetry transformations used to generate equivalent atoms:
−x + 1/2, −y + 1/2, −z + 1

Figure 5:
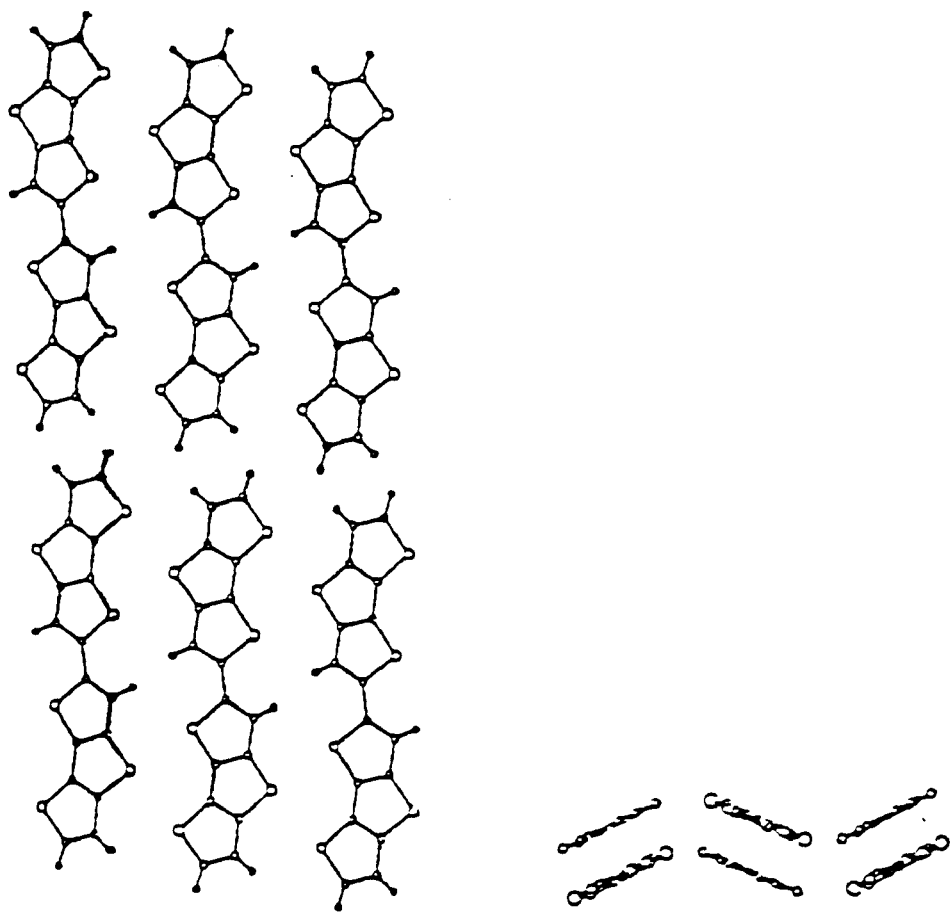
FIG. 5 shows packing views in a BDT crystal.

In each crystal unit cell, there are four molecules packing in a unique way that differs from both 6T and pentacene. Surprisingly, instead of herringbone packing, the BDT molecules packed more planar than either pentacene (which has a herringbone angle of 54°) or 6T (which has a herringbone angle of 66°) (see FIG. 5). The BDT molecules, in fact, pack each other face to face to form stacks with an angle of between two adjacent stacks. The driving force for this unique packing may be contributed from its advanced fused thiophene system and its sulphur atom's self-recognition.

Comparing the minimum distance between two molecules for the three materials, it is noted that the BDT has the shortest π(A)–π(B) distance (3.56 Å) compared with 3.71 Å for pentacene and 3.82 Å for 6T, giving BDT a record close packing molecular system. The π(A)–π(B) stack distance is crucial to determine how strongly and how closely the parallel π systems will interact with each other; a shorter π stack distance should favour higher charge mobility. In the BDT system, the shortest distance is between sulphur atoms of two tilted molecules, being 3.39 Å. The invention exploits this phenomenon in processable organic thin films deposited by vapour and solution methods and is readily extended to include oligomers, polymers and precursor materials.

Optoelectronic properties and field effect mobility

Thin film transistors (TFTs) based on conjugated organic semiconductors are envisioned as the key component of low-cost, large-area electronics on flexible plastic substrates. The two most important material parameters for TFT applications are the field-effect mobility $F_{FE}$ and the ON/OFF ration, i.e., the ratio of the current in the ON state of the TFT to that in the OFF state. To obtain high carrier mobilities at the interface between the thin organic film and the gate dielectric, the film has to be highly crystalline with strong wavefunction overlap between adjacent molecules in the plane of the film. Intermolecular ordering is most easily achieved if a short-chain conjugated oligomer or a molecular semiconductor (α-6T (reference 7), Cu-Pu (reference 19), $C_{60}$ (reference 20)) is deposited by vacuum sublimation. The inventors considered that fused ring compounds, which have less conformational freedom than the prototype oligothiophenes (see reference 19) might yield strong inter- and intramolecular π overlap. It is worth mentioning, however, that with conjugated polymers processed from solution a high degree of order can be obtained by making use of self-organisation mechanisms (see reference 20).

For many memory and display applications a high ON/OFF ratio exceeding 10 is an even more important requirement than a high mobility. It requires a low extrinsic doping level. Most organic TFTs yield relatively low ON/OFF ratios of $10^{31}$–$10^6$ (see references 8, 20, 21). An ON/OFF ratio of $10^8$ has been claimed for pentacene TFTs, which require, however, a voltage range of 200 V, too large to switch between ON and OFF states (see reference 12). So far, the sharpest turn-on characteristics with ON/OFF ratios of $10^6$–$10^7$ have been reported for carefully purified α-6T (see reference 22).

TFTs comprising a fused ring compound of this invention, bis (dithienothiophene) (BDT) have exceptionally high ON/OFF ratios of up to $10^8$ with sharp threshold characteristics. Field-effect mobilities are 0.02–0.05 cm²/Vs. The TFT substrates were highly doped Si wafers with 2000 Å $SiO_2$ gate oxide and interdigitated Au source/drain contacts. The surface of the $SiO_2$ was prepared so as to be hydrophobic by treating it with a solution of hexamethyldisilazane/chloroform (1:2) at $70^1$C. for 3 h. 100–200 nm thick BDT films were deposited by vacuum sublimation at a pressure of $1$–$2 \times 10^{-6}$ Torr. The substrate temperature and evaporation rate were varied between room temperature and ≈130° C. and r=0.2–10 Å/s, respectively. Optimum TFT performance was obtained for T≈100° C. and r≈3 Å/s. The TFT characteristics were measured with an HP 4145B parameters analyser under a dry $N_2$ atmosphere.

Figure 6:
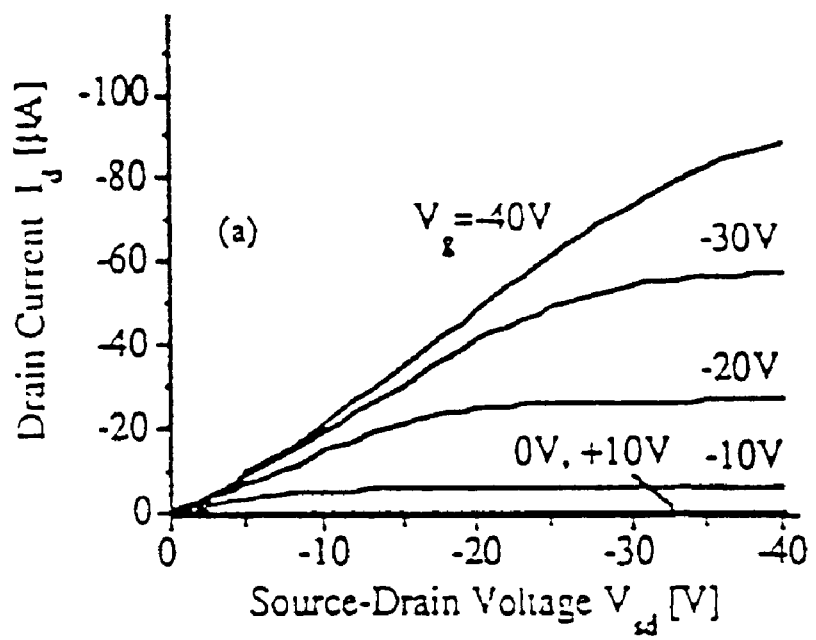
FIG. 6 shows output (a) and transfer characteristics (b) of a BDT TFT deposited at 100° C. (channel length L=20 Fm, channel width W=1 cm, BDT thickness=200 nm)
Figure 6:
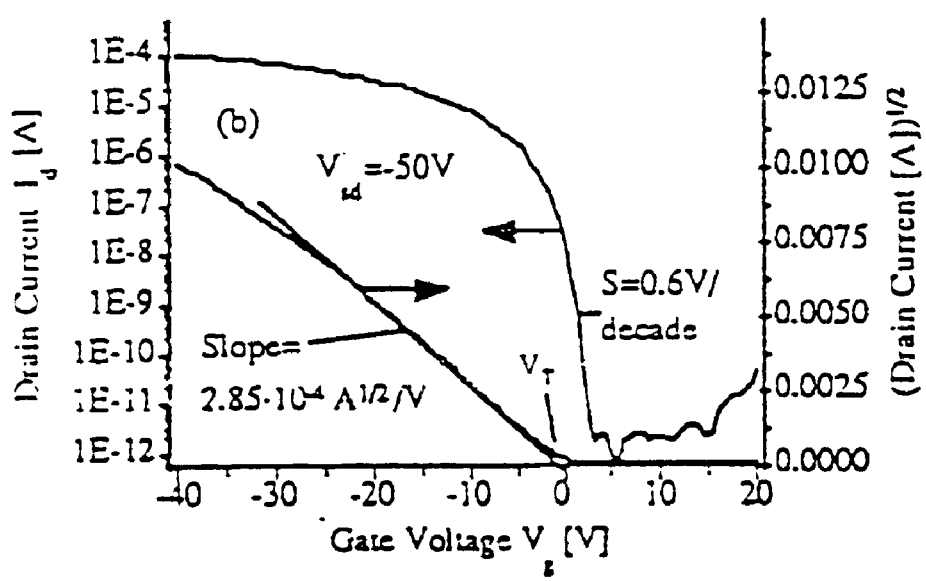

FIG. 6 shows the output (a) and transfer (b) characteristics of a typical BDT TFT deposited at 100° C. As with most other conjugated organic materials, BDT is a p-type semiconductor and the devices operate in the accumulation mode. A small reverse gate bias of 2–6 V is sufficient to turn the channel off ($I_{OFF}$=2–3 pA), which implies that the material is only slightly p-doped. Typical ON/OFF ratios over a gate voltage range of 40 V are $10^7$, but on some samples ON/OFF ratios up to $10^8$ have been obtained (see FIG. 6). The turn-on characteristics are sharp, with a small subthreshold slope $S=(d(\log I_{sd})/dV_g)^{-1}$ of 0.6 V/decade. These are believed to be the best ON/OFF characteristics reported for an organic TFT. They are comparable to those of an a-Si TFT (see reference 23).

Charge carrier mobilities, however, are still an order of magnitude lower than for α-Si. From the transfer characteristics in the saturation regime the mobility is extracted according to the following equation (see reference 24):

$$I_{sd} = \frac{W \cdot C_i}{2 \cdot L} \mu_{FET}^{sat} \cdot (V_g - V_T)^2$$

in which the insulator capacitance $C_i$=16.9 nF/cm². The experimental characteristics are quadratic only in the range 5 V<|Vg|<20 V and exhibits poor current saturation at higher gate voltages. Within the quadratic range, values of $F^{sat}_{FE}$= 0.02–0.05 cm²/Vs are obtained under optimised deposition conditions (substrate temperature, 0.1001 C and deposition rates 1–3 Å/s). The threshold voltage is low, $|V_T|$<5 V. A significant dependence of the mobility on the growth temperature was observed. TFTs grown at room temperature exhibit mobilities, which are lower by about an order of magnitude than at 100° C. The temperature cannot be increased much above 1001 C. because the sticking coefficient of BDT on $SiO_2$ becomes small and the films become discontinous. No deposition on the substrate occurs above 130° C. This behaviour is similar to that observed for benzodithiophene and has been explained by an increase of the grain size at elevated temperatures (see reference 8).

The TFT characteristics in FIG. 6 reveal some non-idealities. Near $V_{ds}$=0, the output characteristics are nonlinear, especially for higher gate voltages. Above $V_q$0.20 V current saturation becomes poor and $V_{sd}$ has to significantly exceed $|V_g-V_T|$ to drive the transistor into saturation. These non-idealities may at least partly be related to a non-ohmic source/drain contact. As discussed below BDT is a high and gap semiconductor to which even a high work-function metal like Au might not form an ohmic contact.

To obtain ON/OFF ratios of $10^8$ the BDT material for the evaporation is purified by recrystallisation and vacuum thermal gradient sublimation. After the growth the films are transferred to a $N_2$ glove box within ≈5 minutes, where the FET characteristics are measured. If stored under dry $N_2$ the TFT characteristics are stable over a period of weeks. However, operation in air results in rapid degradation. If the channel is turned on in air, $I_{sd}$ rapidly increases after a few minutes of operation and roughening around the Au hole-injecting source electrode is observed under an optical microscope, whereas the drain electrode remains intact. By Dektak profilometry the thickness of the Au source electrode is found to decrease in time (from initially 150 nm to about 40 nm after 2-14 3 hours of operation. The Dektak results unambiguously indicate that in spite of the high reduction potential and inertness of Au, the electrochemical reaction and/or electromigration occurs at the contact between BDT and the hole-injecting Au electrode. The reaction only occurs in the presence of water and/or $O_2$ and may also be related to the presence of sulphur in BDT. This contact instability, which may be solved by a different source/drain metallisation or by encapsulation, has so far prevented study of the stability of BDT itself against doping in air.

Figure 7:
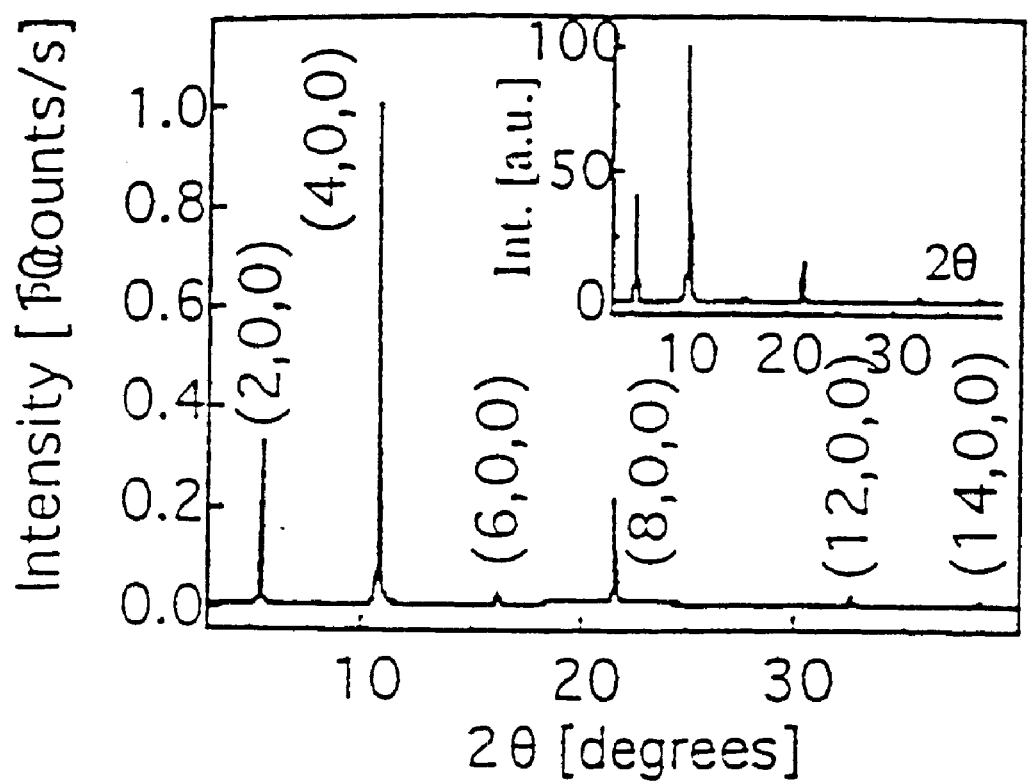
FIG. 7 shows the 0–2θ diffraction pattern of a 250 nm BDT film on SiO$_2$ deposited at 0.100° C. measured with Cu Kα radiation—the insert shows a theoretical simulation of the pattern using the Cerius$^2$Molecular Simulations program—it assumes the single crystal structure of BDT and a preferential orientation of the grains with the bc plane of the nit cell in the substrate plane.

Since the molecular order of the film is crucial for the carrier transport in the TFT the structure of the polycrystalline BDT films have been investigated by X-ray diffraction (XRD). FIG. 7 shows a 6–2θ diffraction pattern of a 250 nm BDT film deposited at ≈100° C. onto $SiO_2$. In this geometry only Braff reflections along the substrate normal can be measured. The observed pattern of sharp reflections can well be explained with the crystal structure of BDT, which has been determined by synchrotron XRD on a single crystal and has been described in detail above. It is sufficient to note that the unit cell is monoclinic with space group C2/c. The cell parameters are a=33.689 Å, α=90°, b=3.883 Å, β=101.093°, c=11.106 Å, γ=90°. Using the single crystal structure the powder diffraction pattern of BDT has been simulated. The simulation shows that in the experimental diffraction pattern of the thin film only (h,0,0) reflections are observed (see inset of FIG. 7). Their positions and intensities are in good agreement with the experimental pattern. These results prove that all grains of the polycrystalline film are oriented with the bc plane of the unit cell parallel to the substrate. In this orientation the long axis of the molecule is close to the substrate normal.

Figure 8:
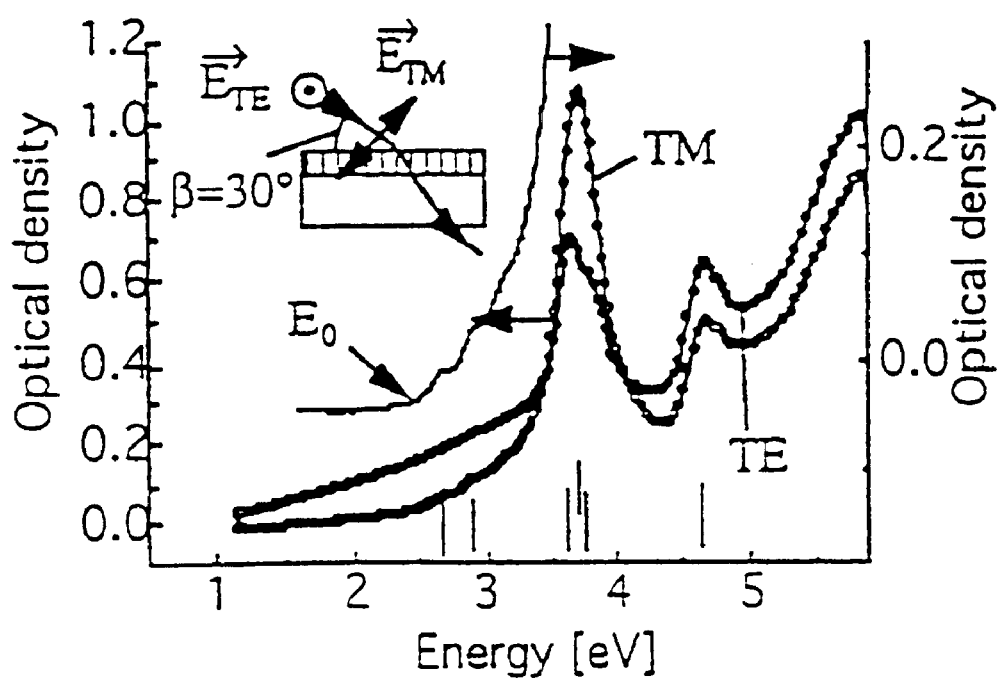
FIG. 8 shows a polarised optical absorption (circles) at an angle of incidence of 60° (see insert) of a 300 Å BDT film deposited at 100° C. on a glass substrate—the spectrum drawn as a solid line shows the enlarged TM spectrum near the onset of absorption.

FIG. 8 shows polarised optical absorption spectra of a BDT film deposited onto a Spectrosil glass substrate held near 100° C. The absorption is characterised by two main peaks at 3.7 eV and 4.7 eV. The spectra exhibit a significant polarisation dependence confirming the high degree of structural order in the film. The absorption at 3.7 eV is stronger by a factor of 2–3 for TM polarisation. Since the molecular axis is close to the substrate normal, this peak must correspond to transitions polarised along the long axis of the molecule. For TM polarisation at least two weaker transitions around 2.65 eV and 2.9 eV below the main absorption at 3.7 eV were reproducibly observed. The onset of absorption is at 2.4±0.2 eV. It was determined by measuring a thick film (not shown) immersed into an inert liquid Teflon solution (Fluorinert FC-104, 3M™) to reduce light scattering. The value is in good agreement with the photoluminescence spectra of BDT films exhibiting a peak at 2.25 eV.

The BDT spectra bear a striking similarity to the polarised absorption spectra of oligothiophenes n-T (n=4,5,6,8) (see reference 25), for which it has been shown that the energy of the strong $\pi$-$\pi^*$ peak along the molecular axis shifts to lower energy with increasing conjugation length of the molecule (4T: $E_{max}$=3.8 eV; 5T: 3.55 eV; 6T: 3.0 eV). In BDT the transition occurs at 3.7 eV which suggests that the conjugation length of the BDT molecule is relatively short, similar to 4T. This is reasonable as Hückel molecular orbital (MO) calculations indicate that in the highest occupied MO (HOMO) and the lowest unoccupied MO (LUMO) there is only small charge density on the centre sulphur atom in each of the two fused ring units making BDT look similar to 4T.

The relatively short conjugation length of the BDT molecule may explain the high ON/OFF ratio of the TFTs. Short chain molecules with a high $\pi$-$\pi^*$ energy gap tend to be more stable against unintentional chemical doping during synthesis and deposition. From capacitance-voltage measurements on metal-insulator-semiconductor (MIS) diodes the extrinsic doping level of BDT is estimated to be on the order of $1-2\times10^{16}$ cm$^{-3}$. This small value is in good agreement with the magnitude of the reverse gate voltage (2–6 V) required to turn the channel off, i.e., deplete the 200 nm thick BDT film. However, it is surprising that such a short chain molecule yields relatively high mobilities of 0.20–0.05 cm$^2$/Vs, higher than mobilities measured in $\alpha$-6T (0.01–0.03 cm$^2$/Vs) (see reference 1) and 4T ($2-5\times10^{-3}$ cm$^2$/Vs) (see reference 25).

The origin of the relatively high mobility must be related to the crystal structure of BDT. As in the oligothiophenes, the long axis of the planar molecule is standing up on the substrate, which favours in-plane carrier transport along the stacking direction of the molecules. However, there is an important difference between the packing of the molecules in BDT and in the oligothiophenes. According to the single crystal XRD results (see above) the packing of nearest-neighbour, face-to-face molecules in BDT is not of the herringbone type. The molecular planes along the $\pi$—$\pi$ stacking direction are strictly parallel to each other whereas in all oligothiophenes they enclose the herringbone angle ($\tau$=66° for $\alpha$-6T) (see reference 26). The coplanar stacking in BDT is likely to result in a stronger $\pi$—$\pi$ overlap between adjacent molecules. The smallest S—S and C—C distances between face-to-face molecules are b=3.39 Å and 3.56 Å, compared to 4.19 Å and 3.56 Å in $\alpha$-6T. This important difference in the crystal structure may explain the relatively high carrier mobilities in spite of the small conjugation length.

BDT is an excellent material for organic TFTs. It yields exceptionally high ON/OFF ratios up to $10^8$ and sharp turn-on characteristics with subthreshold slope of S=0.6 V/decade, comparable to $\alpha$-Si TFTs. The relatively high mobilities (0.02–0.05 cm$^2$/Vs) are explained by the coplanar stacking of the BDT molecules. Further improvement of the carrier mobility may be achieved by improving the carrier injection at the source/drain contacts and extending the conjugation length using dithienothiophene as a building block.

Experimental details

Dithieno[3,2-b:2',3'-d]thiophene (2 ($R_1$=$R_2$=$R_3$=$R_4$=H)) was synthesised according to a published method starting with 3-bromothiophene (see reference 15).

m.p. 66–68° C. $^1$NMR (CD$_2$Cl$_2$, 250 MHz): $\delta$ 7.33 (2 H, d, J 5.2), 7.41 (2 H, d, J 5.2). $^{13}$C NMR (CD$_2$Cl$_2$, 100 MHz): $\delta$ 121.0, 126.2, 131.0, 141.9.

Bis(dithieno[3,2-b:2',3'-d]thiophene) (5 ($R_1$=$R_2$=$R_3$=H)): Butyl lithium (1.6 M, 1.17 mmol) was added into a solution of 2 ($R_1$=$R_2$=$R_3$=H) (230 mg, 1.17 mmol) in dry THF (5 ml) at −78° C. slowly. After being stirred for one hour, an organolithium solution was added via a cannular tube into a refluxing solution of ferric acetylacetonate [Fe(acac)$_3$] (413 mg, 1.17 mmol) in THF (5 ml). The dark red mixture was refluxed under argon for 2 hours, and then poured into water (100 ml) to give a brown solid. After filtration, the solid was washed with dilute HCl (2%), water, dilute Na$_2$CO$_3$ (10%) and acetone respectively. The final light brown powder was recrystallised from toluene twice to give gold like flake crystals (130 mg, 57%).

m.p. 3171C (DSC, 10° C./min, N$_2$); $^1$NMR (THF-d$_8$, 250 MHz): $\delta$ 6.95 (2H, d, J 5.2), 7.51 (2 H, d, J 5.2), 7.85 (2H, s); FTIR (KBr) $v_{max}$/cm$^{-1}$ 3070 s, 1670 m, 1465 m, 1427 m, 1364 s, 1185 m, 1072 m, 897 m, 796 s, 688 s, 593 s; UV $\lambda_{max}$: 392 nm; Found: C, 49.2%; H, 1.51%; HRMS: 389.8794(M$^+$), C$_{16}$H$_6$S$_6$ requires C, 49.2%; H, 1.55%; M$^+$389.8794.

X-ray data collection and structure solution

Data were collected at the Daresbury Synchrotron radiation source, station 9.8, using a Siemens SMART COD diffractometer (courtesy of Dr N. Feeder and Dr W Clegg). A frame width of 0.30 was used, with a 2s exposure per frame. All data were collected at 160K. Of a total of 1272 collected reflections, 813 were independent [R(int)=0.0429; (3.58≤q≤26.89)].

The structure was solved by direct methods (S1R92) and refined by full-matrix least-squares on $F^2$ (SHELXL93) to final values of R1 [I>2s(I)]=0.047 and wR2=0.1265, S=1.112 {w=1/[\s$^2$(Fo$^2$)+(0.0977P)$^2$], where P=(Fo$^2$+2 Fc$^2$)/3}.

The largest peak and hole in the final difference map were 0.445 and −0.490 e Å$^{-3}$.

EXAMPLES

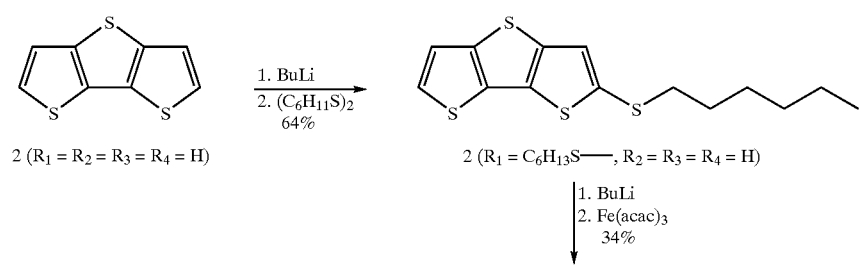

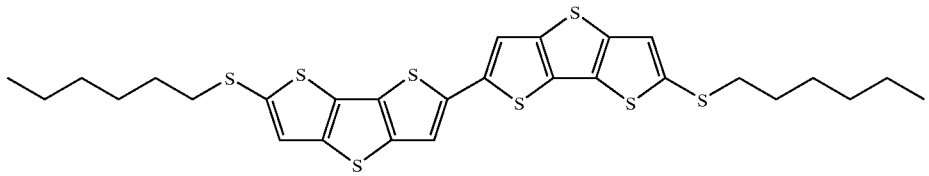

5 (R$_1$ = C$_6$H$_{13}$S—, R$_2$ = R$_3$ = H)

Preparation of 2-(1-thiohexyl)-dithienothiophene 2 (R$_1$=C$_6$H$_{13}$S—, R$_2$=R$_3$=R$_4$=H)

The method Ng was followed (see reference 28). Dithienothiophene 2 (R$_1$=R$_2$=R$_3$=R$_4$=H) (1.178 g, 6.0 mmol) was dissolved in dry THF (5 cm$^3$) and stirred under argon at −78° C., n-Butyl lithium (4 cm$^3$, 1.5 M, 6.0 mmol) was added dropwise with stirring. During this addition a yellow suspension formed and the mixture was allowed to warm to r.t. After stirring at r.t for a further 45 min. the mixture was cooled to 0° C. and dihexyl disulfide (1.41 cm$^3$, d 0.95, 6.0 mmol) was added dropwise. The mixture was stirred at r.t. for 1 h. then refluxed for 45 min. before being cooled and poured into water (20 cm$^3$). The products were extracted with ether (3×50 cm$^3$), washed with sodium hydroxide solution (50 cm$^3$, 2%) then water before drying (Na$_2$SO$_4$) and evaporation to give a dark green oil. This was purified by vacuum packed column chromatography (20×4.5 cm silica with hexane) to give the title compound 2 (R$_1$=C$_6$H$_{13}$S—, R$_2$=R$_3$=R$_4$=H) (1.202 g, 64%); R$_f$(hexane) 0.28; δ$_H$ 0.89 (3H, t, J6.9), 1.23–1.48 (6H, m), 1.66 (2H, pentet, J7.3), 2.85 (2H, t, J7.3), 7.27 (1H, d, J5.3), 7.33 (1H, s), 7.35 (1H, d, J5.3); δ$_C$ 14.0 (CH$_3$), 22.6 (alkyl), 28.1 (alkyl), 29.5 (alkyl), 31.4 (alkyl), 39.4 (S—CH$_2$), 120.7 (ArCH), 126.2 (ArCH), 131.0 (ArCH), 133.4 (Ar q), 135.8 (Ar q), 140.3 (Ar q) and 141.4 Ar q); m/z 314 (M$^+$+2, 15%), 313 (M$^+$=1, 11), 312 (M$^+$, 65), 230 (18), 229 (20), 228 (100), 227 (66), 196 (22), 183 (34), 152 (24), 151 (18), 69 (19), 43 (53) and 41 (56); m/z calc $^{12}$C$_{14}$$^1$H$_{16}$$^{32}$S$_4$ 312.001348, found 312.013500; u max/cm$^{-1}$ (CDCl$_3$) 3090 w, 2958 s, 2930 s, 2858 m, 2359 w, 2246 w, 1466 m, 1360 s, 1189 w, 1153 w, 1088 m, 1001 w, 964 w, 829 m and 604 m.

Preparation of 2,2'-dithiohexyl-bisdithienothiophene (DTH-BDT) 5 (R$_1$=C$_6$H$_{13}$S—, R$^2$=R$^3$=H).

2-(1-thiohexyl-dithienothiophene 2(R$_1$=C$_6$H$_{13}$S, R$_2$=R$_3$=R$_4$=H) (200 mg, 0.64 mmol) was dissolved in dry THF (4 cm$^3$) and stirred under nitrogen at 0° C., n-Butyl lithium (0.40 cm$^3$, 1.6 M, 0.64 mmol) was added dropwise with stirring. During this addition the mixture turned green and retained this colour on stirring at r.t for 40 min. Ferric acetylacetonate (226 mg, 0.64 mmol) was suspended in dry THF (4 cm$^3$) and refluxed under nitrogen. The lithiated dithienothiophene was added via syringe and refluxed for 1 h. During this time the mixture turned dart red and some precipitation was observed. The mixture was cooled and poured into water (40 cm$^3$), the solids were filtered and washed with 2% aqueous HCl (2×50 cm$^3$), water (40 cm$^3$), aqueous Na$_2$CO$_3$ then acetone (3×30 cm$^3$). Recrystallisation of the dark brown filter cake was attempted in toluene. This was difficult due to the intense dark brown coloration of the suspension in which dissolution was difficult to define. The mixture was allowed to cool slowly then the solids were filtered off to give a lighter brown filter cake. This was dissolved in THF and residual solids (presumably Fe(acac)$_2$) were filtered off. The THF was evaporated off and a further recrystallisation from toluene gave a gold solid (68 mg, 34%) which was found to be the title compound; δ$_H$ (400 MHz, THF-d8) 0.91 (3H, t, J7.0), 1.30–1.38 (6H, m), 1.47 (2H, pentet, J7.3), 2.92 (2H, t, J7.4), 7.44 (1H, s), 7.60 (1H, s), m/z 624 (M$^+$+2, 1%), 622 (M$^+$, 2), 537 (1), 506 (2), 421 (4), 277 (7), 199 (10), 149 (15), 135 (15), 121 (17), 91 (62), 81 (65), 69 (100) and 55 (40); m/z calc. $^{12}$C$_{28}$$^1$H$_{30}$$^{32}$S$_8$ 622.011318, found 622.011300; n$_{max}$/cm$^{-1}$ (KBr) 2954 m, 2924 s, 2854 m, 1466 m, 1426 m, 1361 s, 1161 w, 1001 w, 924 m, 788 s, 688 m, and 594 m; C$_{28}$H$_{30}$S$_8$ requires C, 53.98; H, 4.85. Found C, 52.68; H, 4.25; Fe, 0.23. The compound was found to sublime at 1.5×10$^{-5}$ Torr/175° C. Approximate field effect mobility was 10$^{-3}$ cm$^2$V$^{-1}$S$^{-1}$; Approximate On/Off ratio 10$^6$.

Preparation of dithienothiophene-2-carboxylic acid 2 (R$_1$=COOH, R$_2$=R$_3$=R$_4$=H).

The method of Gronowitz et al (see reference 28) was followed. Dithienothiophene 2 (R$_1$=R$_2$=R$_3$=R$_4$=H) (368 mg, 1.88 mmol) was dried by heating under vacuum in a Schlenk tube. After purging with nitrogen, dry THF (4 cm$^3$) was added and the resulting solution stirred at −78° C. n/Butyl lithium (1.175 cm$^3$, 1.60 M, 1.88 mmol) was added dropwise to the cold stirred solution which turned cloudy green after stirring for 10 min., but gave a transparent green solution on warming to r.t. The solution was stirred at r.t. for a further 40 min. then cooled to around −40° C. (not so cold as to precipitate out the lithiodithienothiophene). Carbon dioxide was added in small lumps to a flask against a fast flow of nitrogen. The flask was then sealed under a nitrogen bubbler and cooled to the −78° C. THF was added to cover the CO$_2$ and the mixture stirred. The cooled lithiodithienothiophene was added dropwise via syringe and a violent reaction was observed resulting in the formation of a yellow suspension. Once addition was complete the mixture was allowed to warm to r.t. during which time the mixture turned to an off white colour. After stirring for a further 30 min. water (30 cm$^3$) was added and the mixture turned to a light green/brown solution. This was washed with ether (2×20 cm$^3$) and the organics discarded. The aqueous layer was acidified by the addition of HCl (10 cm$^3$, 5 M) which precipitated out a fine yellow solid. Recrystallisation was attempted in 33% acetic acid. A fine, insoluble suspension remained after heating and this was left to further crystallise overnight to give the title compound as a fine yellow/green powder (286 mg, 61%), δ$_H$ 7.31, (1H, d, J5.1), 7.56 (2H, d, J5.1), 7.94 (1H, s); v max/cm$^{-1}$ (KBr) 3090 m, 2823 m, 2559 m, 1652 s, 1504 s, 1470 w, 1428 s, 1311 s, 1265 m, 1164 m, 928 s, 750 s, 716 s and 602 s; m.p. 276° C. (sublimes) m.p. (lit. reference 29) 275–277° C.)

Preparation of the dithienothiophene-2-carboxylic acid complex 12 with tris94,5-dihydroimidazol-2-yl)benzene Dithienothiophene-2-carboxylic acid 2 (R$_1$=COOH, R$_2$=R$_3$=R$_4$=H) (240 mg, 1 mmol) and tris(4,5-dihydroimidazol-2-yl)benzene (93 mg, 0.33 mmol) were dissolved by refluxing in a mixture of 20 cm$^3$ EtOH and 150 cm$^3$ of CHCl$_3$. This gave a turbid solution which was filtered whilst hot through a fine sinter and allowed to cool and stand overnight. Very little precipitation was observed and so the volume of the mixture was evaporated down to 40 cm$^3$ and cooled in the freezer. Again very little precipitation was observed and so the solvents were evaporated down to 20 cm$^3$ at which point the products rapidly precipitated from solution and would not re-dissolve until the original quantities of solvents were added and the mixture refluxed. The mixture was evaporated to dryness then re-dissolved in the ethanol and chloroform in the same fashion as before. On this occasion, very careful evaporation at 50° C. close to atmospheric pressure gave rise to a small quantity of precipitate once the solvent volume was reduced to about 30 cm$^3$. On cooling the solution and then leaving it to stand in the freezer overnight a large quantity of the complex 12 had precipitated had developed. This was filtered off to give 189.1 mg, 57%, m.p. 265° C. (decomp.); $\delta_H$ (CD$_3$OD, 500 MHz) 7.38 (3H, d, J5.1), 7.59 (3H, d, J5.1), 7.84 (3H, s) and 8.48 (3H, s). $v_{max}$/cm$^{-1}$ (KBr) 3086, 2924, 2706, 1582.

Preparation of the complex 13

2'-Octyldithienothiophene-2-carboxylic acid (130 mg, 0.369 mmol) and 1,3,5-tris(4,5-dihydroimidazol-2-yl) benzene (34.7 mg, 0123 mmol) were dissolved in hot ethanol (30 ml)/dichloromethane (20 ml). The yellow solution was filtered whilst hot, concentrated in vacuum to about 35 ml until a solid started to precipitate from solution, once more heated to reflux and left to stand at −20° C. for 2 d. The yellow precipitate was collected by suction filtration, washed with ethanol (10 ml) and dried at 60° C./10$^{-6}$ mbar. Yield of 13 42 mg (25%). As suspected, the octyl substituent depresses the melting point of the compound to about 160–165° C. Upon melting, a mesophase with relatively low viscosity can be detected $^1$H NMR (500 MHz, CDCl$_3$, 1.1 mg/0.8 ml): δ=0.88 (t, J=7.0 Hz, CH$_3$), 1.23–1.43 (m), 1.73 (qui., J=7.4 Hz, CH$_2$), 2.90 (t, J=7.4 Hz, CH$_2$), 4.22 (s, NCH$_2$), 6.98 and 7.80 (s, thiophene-CH), 10.00 (s; C$_6$H$_3$), 12.8 (br.s, NH); IR (KBr):$v_{max}$/cm$^{-1}$ 3426 (m), 2925 (m), 1582 (s), 1500 (m), 1372 (s), 1288 (m), 773 (m), 694 (m); C$_{66}$H$_{78}$N$_6$O$_6$S$_9$ (1339.92): Calc. C, 59.16; H, 5.87; N, 6.27. Found: C, 58.89; H, 5.82; N, 6.37.

Octanoyl-dithienothiophene 2 (R$_1$=COC$_7$H$_{15}$, R$_2$=R$_3$=R$_4$=H).

Dithienothiophene 2 (R$_1$=R$_2$=R$_3$=R$_4$=H) (765 mg, 3.90 mmol) was dissolved in dry dichloromethane (35 cm$^3$) and the solution was ice-cooled before AlCl$_3$ (790 mg, 5.92 mmol) was added in one portion yielding a dark mixture. A solution of octanoyl chloride (1.00 g, 6.02 mmol) in dichloromethane (20 cm$^3$) was added dropwise over a 20 minute period and the mixture was then allowed to stand at room temperature for a further thirty minutes. It was then added to ice and the mixture was acidified with dilute hydrochloric acid (100 cm$^3$). Additional dichloromethane (100 cm$^3$) was added and the layers separated. The organic layer was washed with water, dried over MgSO$_4$ and concentrated. Column Chromatography (hexane—30% dichloromethane/hexane) afforded 790 mg (63%) of the title compound. An analytical sample may be prepared by recrystallisation from a mixture of dichloromethane and methanol. R$_f$ 0.31 (1:1 dichloromethane/hexane); m.p. 130–131° C.; $^1$H (250 MHz, CDCl$_3$) δ 0.89 (3H, t, J6.5, CH$_2$CH$_3$); 1.25 (8H, br s, CH$_2$CH$_2$CH$_2$); 1.78 (2H, m, CH$_2$CH$_2$CO); 2.93 (2H, t, J7.5, CH$_2$CO); 7.32 (1H, d, J5.0, Dt-H); 7.52 (1H, d, J5.0, Dt-H); 7.91 (1H, s, Dt-H); $^{13}$C (100 MHz, CDCl$_3$) δ 14.1; 22.6; 25.0; 29.1; 29.3; 30.9; 31.7; 39.0; 120.9; 125.5; 129.0; 141.4; 144.4; 144.9; 193.7; v (cm$^{-1}$, KBr) 600, 702, 1191, 1364, 1466, 1493, 1644 (C=O), 2925; Calc. for C$_{16}$H$_{18}$S$_3$O C, 59.6; H, 5.6. Found: C, 59.2; H, 5.6.

α-Octyl-dithienothiophene 2 (R$_1$=C$_8$H$_{17}$, R$_2$=R$_3$=H)

Aluminium chloride (82 mg, 0.615 mmol) was dissolved in anhydrous diethyl ether (6 cm$^3$) and the solution was added slowly to an ice-cooled mixture of lithium aluminium hydride (103 mg, 2.71 mmol) in anhydrous diethyl ether (6 cm$^3$). A solution of 2 (R$_1$=COC$_7$H$_{15}$, R$_2$=R$_3$=R$_4$=H) (89 mg, 0.276 mmol) in dry toluene (7 cm$^3$) was added and the mixture stirred for one hour. TLC analysis (1:1 dichloromethane/hexane) showed the complete disappearance of starting material and two new spots (R$_f$=0.69, 0.22). The lower of these was putatively ascribed to the intermediate alcohol. Additional AlCl$_3$ (39 mg, 0.29 mmol) was added and the mixture stirred for a further hour. Ethyl acetate (2 cm$^3$) and dilute hydrochloric acid (4 cm$^3$) were sequentially added and the grey mixture filtered. The filter-

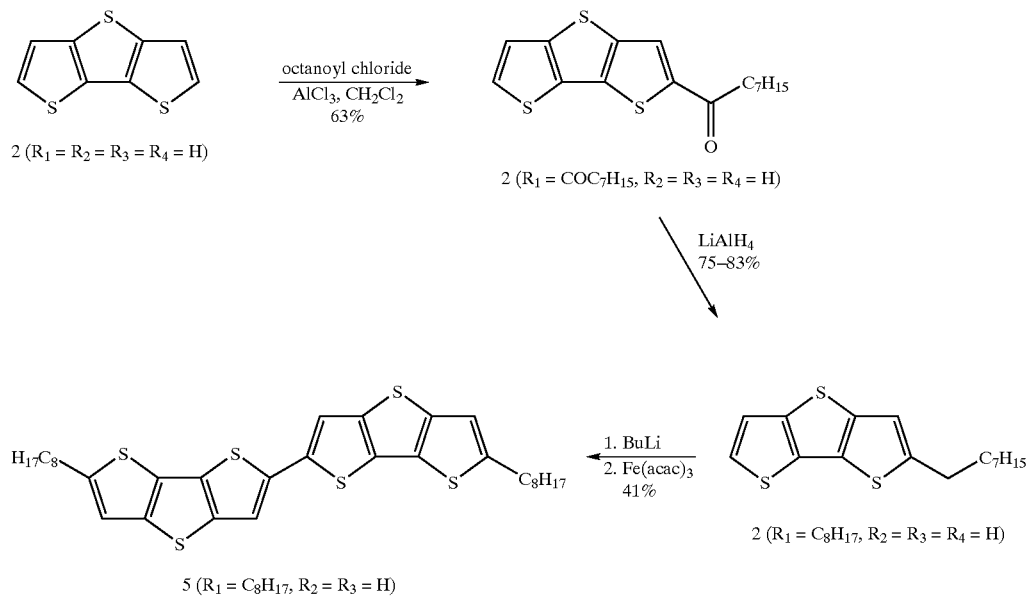

cake was washed well with additional toluene and the layers separated. The organic layer was dried over MgSO$_4$ and concentrated under vacuum. Column chromatography using hexane as an eluent afforded 64 mg (75%) of the title compound R$_f$ 0.38 (hexane).

Bis(octyldithienothiophene) 5 (R$_1$=(C$_8$H$_{17}$, R$_2$=R$_3$=H)

Dimerisation of 2 (R$_1$=C$_8$H$_{17}$, R$_2$=R$_3$=H) according to the procedure described above for 5 gave the title compound m.p. 195–196° C. in 41% yield. $^1$H NMR (d8-THF, 400 MHz) δ 0.91 (6H, t, J7), 1.26–1.49 (2OH, m), 1.67–1.81 (4H, m under THF signal), 2.96 (4H, t, J7), 7.1 (2H, s) and 7.56 (2H, s). Approximate field effect mobility was 10$^{-2}$ cm$^2$V$^{-1}$s$^{-1}$.

References

1. J. J. M. Halls, C. A. Walsh, N. C. Greenham, E. A. Marseglia, R. H. Friend, S. C. Moratti and A. B. Holmes, *Nature*, 1995, 376, 498–500.
2. N. C. Greenham, S. C. Moratti, D. D. C. Bradley, R. H. Friend and A. B. Holmes, *Nature*, 1993, 365, 628–630.
3. F. Garnier, R. Hajlaoui, A. Yassar and P. Srivastava, *Science*, 1994, 265, 1684–1686.
4. G. Horowitz, D. Fichou, X. Z. Peng, Z. G. Xu and F. Garnier, *Solid State Commun.*, 1989, 72, 381.
5. F. Garnier, *Pure & Appl. Chem.*, 1996, 68, 1455–1462.
6. H. E. Katz, *J. Mater. Chem.*, 1997, 7, 369–376.
7. Z. Bao, A. Dodabalapur and A. J. Lovinger, *Appl. Phys. Lett.*, 1996, 69, 4108–4110.
8. J. G. Laquindanum, H. E. Katz, A. J. Lovinger and A. Dodabalapur, *Adv. Mater.*, 1997, 9, 36.
9. G. Horowitz, D. Fichou, X. Peng and F. Garnier, *Synth. Met.*, 1991, 41–43,1127.
10. A. R. Brown, A. Pomp, D. M. Deleeuw, D. B. M. Klaassen, E. E. Havinga, P. Herwig and K. Mullen, *J. Appl. Phys.*, 1996, 79, 2136–2138.
11. A. R. Brown, A. Pomp, C. M. Hart and D. M. de Leeuw, *Science*, 1995, 270, 972–974.
12. D. J. Gundlach, Y. Y. Lin, T. N. Jackson, S. F. Nelson and D. G. Schlom, *Ieee Electron Device Lett.*, 1997, 18, 87–89.
13. Y. Y. Lin, D. J. Gundlach and T. N. Jackson, *54th Annual Device Research Conference Digest*, 1996, 80.
14. J. G. Laquindanum, H. E. Katz, A. J. Lovinger and A. Dodabalapur, *Chem. Mater.*, 1996, 8, 2542.
15. F. de Jong and M. J. Janssen, *J. Org. Chem.*, 1971, 36, 1645–1648.
16. F. R. Lispett, *Can. J. Phys.*, 1957, 35, 284.
17. M. Helbig and H.-H. Horhold, *MakromoL Chem.*, 1993, 194, 1607–1618.
18. R. Cervini, X. C. Li, G. W. C. Spencer, A. B. Holmes, S. C. Moratti and R. H. Friend, *Synth. Met.*, 1997, 84, 359–360.
19. F. Gamier, R. Yassar, R. Hajlaoui, G. Horowitz, F. Deloffe, B. Servet, S. Ries and P. Alnot, *J. Am. Chem. Soc.*, 1993, 115, 8716.
20. Z. Bao, A. J. Lovinger and A. Dodabalapur, *Appl. Phys. Lett.*, 1996, 69, 3066–3068.
21. R. C. Haddon, T. Siegrist, R. M. Fleming, P. M. Bridenbaugh and R. A. Laudise, *J. Mater. Chem.*, 1995, 5, 1719–1724.
22. A. Dodabalapur, L. Torsi and H. E. Katz, *Science*, 1995, 268, 270–271.
23. C. Chen and J. Kanicki, *IEEE Electron Device Letters*, 1996, 17, 437.
24. M. S. Shur, M. Hack and J. G. Shaw, *J. Appl. Phys.*, 1989, 66, 3371.
25. R. Hajlaoui, G. Horowitz, F. Garnier, A. Arcebrouchet, L. Laigre, A. Elkassmi, F. Demanze and F. Kouki, *Adv. Mater.*, 1997, 9, 389.
26. F. Garnier, G. Horowitz, D. Fichou and A. Yassar, *Synth. Met,* 1996, 81, 163–171.
27. A. Kraft and F. Osterod *J. Chem. Soc. Perkin Trans.* 1, 1998, 1019.
28. S. C. Ng, H. S. O. Chan, H. H. Huang and B. S. H. Seow, *J. Chem. Res. (M)*, 1996, 1282.
29. D. M. Tanner, L. Zhang, M. Vigneswaran and P. Kandanarchchi, *J. Org. Chem.*, 1995, 60, 4481.

What is claimed is:

1. A light-emitting device, including a polymer comprising a dithieno[3,2-b:2',3'-d]thiophene repeating unit.
2. A light-emitting device according to claim 1, comprising a light-emitting diode.
3. A light-emitting device according to claim 1, wherein the polymer is solution processable.
4. A light-emitting device according to claim 3, wherein the polymer includes a solubilising side chain.
5. A light-emitting device according to claim 4, wherein the side chain carries alkyl, aryl or heterocyclic substituents.
6. A light-emitting device according to claim 1, wherein the polymer additionally comprises one or more non-fused thiophene moieties and/or units.
7. A light-emitting device according to claim 1, wherein the polymer includes a repeat unit having general formula 6:

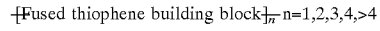

where n=1,2,3,4,>4 and the fused thiophene building block is selected from the group consisting of the repeat units having general formula 7 to 11:

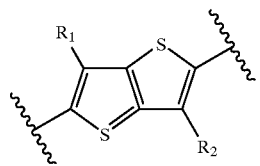

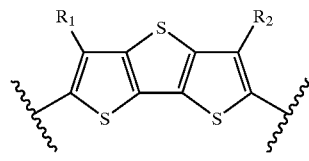

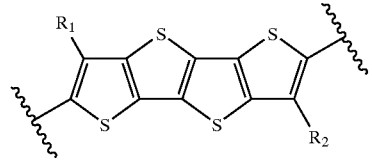

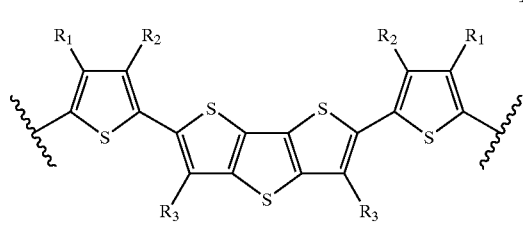

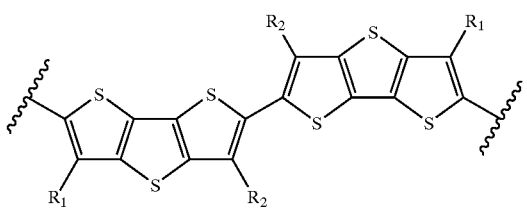

wherein $R_1$, $R_2$ and $R_3$ are selected from any combination of H, $(CH_2)_nCH_3$, $O(CH_2)_nCH_3$, $S(CH_2)_nCH_3$, or a branched chain derivative carrying aryl, alkyl or heterocyclic substituents or other solubilising side chain alkyl, aryl or heterocyclic substituents and where $R_1$ may also be COOH, triazole, tetrazole or a derivative thereof.

8. A light-emitting device according to claim 1, wherein the polymer comprises one fused thiophene coupled to another fused thiophene wherein the fused thiophene is dithieno[3,2-b:2',3'-d]thiophene.

9. A method for making a light-emitting device including a polymer comprising a dithieno[3,2-b:2',3'-d]thiophene repeating unit, comprising depositing the polymer on a substrate.

10. A method according to claim 9, wherein deposition is carried out from solution.

11. A method of transporting or injecting charge in a light-emitting device using a polymer comprising a dithieno[3,2-b:2',3'-d]thiophene repeating unit.

12. A method according to claim 11, wherein the light-emitting device comprises a light-emitting diode.

13. A method according to claim 11, wherein the polymer is solution processable.

14. A method according to claim 13, wherein the polymer includes a solubilising side chain.

15. A method according to claim 14, wherein the side chain carries alkyl, aryl or heterocyclic substituents.

16. A method according to claim 11, wherein the polymer additionally comprises one or more non-fused thiophene moieties and/or units.

17. A method according to claim 11, wherein the polymer comprises one fused thiophene coupled to another fused thiophene wherein the fused thiophene is dithieno[3,2-b:2',3'-d]thiophene.

18. A polymer comprising one fused thiophene coupled to another fused thiophene wherein the fused thiophene is dithieno[3,2-b:2',3'-d]thiophene and additionally comprising one or more non-fused thiophene moieties and/or units.

19. A polymer according to claim 18, wherein the polymer is solution processable.

20. A polymer according to claim 19, wherein the polymer includes a solubilising side chain.

21. A polymer according to claim 20, wherein the side chain carries alkyl, aryl or heterocyclic substituents.

22. A method for the production of a polymer as defined in claim 18, which method comprises coupling one fused thiophene derivative to another fused thiophene derivative wherein the fused thiophene is dithieno[3,2-b:2',3'-d]thiophene.

23. A thin film transistor including a polymer comprising a dithieno[3,2-b:2',3'-d]thiophene repeating unit.

24. A method of transporting or injecting charge in a thin film transistor using a polymer comprising a dithieno[3,2-b:2',3'-d]thiophene repeating unit.

25. A method for making a thin film transistor including a polymer comprising a dithieno[3,2-b:2',3'-d]thiophene repeating unit, comprising depositing the polymer on a substrate.

* * * * *